United States Patent
Sandoval Borquez et al.

(10) Patent No.: US 11,512,354 B2
(45) Date of Patent: Nov. 29, 2022

(54) NON-INVASIVE METHOD FOR THE EARLY DIAGNOSIS OF GASTRIC CANCER USING AS A BIOMARKER THE METHYLATION LEVELS IN THE DNA SEQUENCE OF MICRORNA-335-5P PROMOTER

(71) Applicant: PONTIFICIA UNIVERSIDAD CATOLICA DE CHILE, Santiago (CL)

(72) Inventors: Alejandra Sandoval Borquez, Santiago (CL); Alejandro Corvalán Rodríguez, Santiago (CL)

(73) Assignee: Pontificia Universidad Catolica de Chile, Santiago (CL)

( * ) Notice: Subject to any disclaimer, the term of this patent is extended or adjusted under 35 U.S.C. 154(b) by 0 days.

(21) Appl. No.: 16/645,250

(22) PCT Filed: Sep. 7, 2018

(86) PCT No.: PCT/CL2018/050084
§ 371 (c)(1),
(2) Date: Mar. 6, 2020

(87) PCT Pub. No.: WO2019/046985
PCT Pub. Date: Mar. 14, 2019

(65) Prior Publication Data
US 2020/0199682 A1 Jun. 25, 2020

(30) Foreign Application Priority Data

Sep. 8, 2017 (CL) .................................. 2289-2017

(51) Int. Cl.
*C12Q 1/6886* (2018.01)
*C12Q 1/6869* (2018.01)
(52) U.S. Cl.
CPC ......... *C12Q 1/6886* (2013.01); *C12Q 1/6869* (2013.01); *C12Q 2600/154* (2013.01)
(58) Field of Classification Search
None
See application file for complete search history.

(56) References Cited

U.S. PATENT DOCUMENTS 9,546,403 B1 * 1/2017 Warren ................. C12Q 1/6883
2011/0177965 A1 7/2011 Hoshen et al.

FOREIGN PATENT DOCUMENTS

WO 2016/022076 2/2016

OTHER PUBLICATIONS

Li, et al., "Methylation-associated silencing of MicroRNA-335 contributes tumor cell invasion and migration by interacting with RASA1 in gastric cancer", Am J. Cancer Res 2014; 4(6):648-662.
Zhang, et al., "Up-regulation of CRKL by microRNA-335 methylation is associated with poor prognosis in gastric cancer", Cancer Cell Int 2017; vol. 17, No. 1, pp. 1-14.
Sandoval-Borquez, et al., "MicroRNA-335-5p in a potential suppressor of metastasis and invasion in gastric cancer", Clincal Epigenetics 2017; vol. 9, No. 1, pp. 1-16.
Zare, et al., "The clinical significance of miR-335, miR-124, miR-218 and miR-484 downregulation in gastric cancer", Molecular Biology Reports, 2018, 10 pages.
Zhang, et al,. "Prognostic value of microRNAs in gastric cancer: a meta-analysis", Oncotarget, 2017, vol. 8, No. 33, pp. 55489-55510.
Wu, et al., "Advances in molecular biomarkers for gastric cancer: miRNAs as emerging novel cancer markers", Expert Reviews in Molecular Medicine 2014, vol. 16, pp. 1-18.
Ma, et al., "Quantification of Plasma miRNAs by Digital PCR for Cancer Diagnosis" Biomarker Insights 2013, vol. 8, pp. 127-136.
He, et al., "The role low microRNA-335 expression in prognosis prediction of human cancers", Journal of Cancer Research and Therapeutics, 2016, vol. 12, No. 2, pp. 1070-1074.
Xu, et al., "MicroRNA-335 acts as a metastasis suppressor in gastric cancer by targeting Bcl-w and specificity protein 1", Oncogene 2012, vol. 31, No. 11, pp. 1398-1407.
Yan, et al., Identification of hsa-miR-335 as a Prognostic Signature in Gastric Cancer, Plos ONE 2012, vol. 7, No. 7, e40037, pp. 1-10.
Yan, et al., "Comparison of Prognostic MicroRNA Biomarkers in Blood and Tissues for Gastric Cancer", Journal of Cancer 2016, vol. 7, No. 1, pp. 95-106.
Li, et al., "The clinical significance of down regulation of mir-124-3p, mir-146a-5p, mir-155-5p and mir-335-5p in gastric cancer tumorigenesis", International Journal of Oncology 2014, vol. 45, pp. 197-208.
International Search Report issued in International Application No. PCT/CL2018/050084, dated Nov. 12, 2018, 6 pages.

* cited by examiner

*Primary Examiner* — Katherine D Salmon
(74) *Attorney, Agent, or Firm* — Hamre, Schumann, Mueller & Larson, P.C.

(57) ABSTRACT

The invention is directed to a method for the early detection of gastric cancer, by detecting the increase in DNA methylation of the promoter region of the microRNA-335-5p in samples obtained non-invasively, preferably in plasma. Thus, it is a contribution for the early detection of gastric cancer, without invasive procedures, with rapid collection of the sample and of the delivery of the results, and of lower cost than the technologies that employ invasive diagnostic techniques to the human and animal body in general.

3 Claims, 1 Drawing Sheet
Specification includes a Sequence Listing.

SEQUENCE LISTING

<160> NUMBER OF SEQ ID NOS: 3

<210> SEQ ID NO 1
<211> LENGTH: 5003
<212> TYPE: DNA
<213> ORGANISM: Human

<400> SEQUENCE: 1

| | | | | | |
|---|---|---|---|---|---|
| ttgcgaaagc | cgtcccctcc | ggctggaatg | ttctttgtct | ctctggtaaa | tgtctattca | 60 |
| tcattcaaga | ccaccttcg | cccctcccct | taattacttc | ctcccctgtg | cgccctcaaa | 120 |
| ttcttgtact | cattcaagca | gtatttatta | ggggccagct | tgtggccgg | caccgtggcg | 180 |
| ggctctgggg | ctacaaaagg | tgaataatac | ttgggctctg | cctctgaggg | ccttacacgt | 240 |
| tagggaggag | tgggtcaact | gccacaaacg | tcgctaggaa | attaaaagga | aaattttaca | 300 |
| aagtggcagt | tcttgtctgt | cttcccctcc | agatggcccg | tgtgttgttt | tcggccggg | 360 |
| gctatttctc | atttatttcg | caccccggt | tcttagtgcc | ctgtaggtgc | taaatcagca | 420 |
| tttgttttcat | gagtgctttt | tctggggca | accagacccc | tgcagaagtg | tacctgtgtt | 480 |
| gtgccagagg | ttctgatgat | aggcttatag | gcggtagttt | cctcagtgtc | cgtgggtcgc | 540 |
| ccccggtccc | gggttggatg | ccccgcggtc | cagcaccgaa | cctttcgggg | tgcagagttg | 600 |
| cagagccgcg | gagggcccgg | gccgtgcgca | gccgaaggga | ggcctgcagc | gcccctctg | 660 |
| gatgcagcgg | gcaccggccg | gccgccccgc | tcacccgctc | gcaccccacg | tttgttcacc | 720 |
| agtatttcag | tttacggtca | gaaaatgaac | acagacactt | cgtgatactc | tacactttc | 780 |
| aaaggcgtaa | gggatgcctt | ttaaaggatt | atggattaga | aaaattcctc | cctctttctt | 840 |
| gtgcctctgg | gcccttgcat | tgtgattcta | tcttacgtaa | ataaagggg | ctttgctctc | 900 |
| ctaattgtgc | ccactgttct | gtgcagcgcg | gaccggcgca | tgcagcgagc | ggggctgcga | 960 |
| gggcgctgct | gtggccaggc | gtctggcatg | ctgaccacgt | cgcgctgctg | taaaggaaac | 1020 |
| ctgccccgcg | cagcggcggt | ggctggagcg | ggagaaaccg | gactttgtgc | aactttggcc | 1080 |
| atagtggcca | tcccatgaat | ctgtttacta | gcttggtggt | gggtccaaca | gagcttgttg | 1140 |
| ctccctagcc | gcttgctcgt | gcccttggtg | gttaccggta | gttaagctta | gggcgcatag | 1200 |
| ggccctcgtg | gctcgccacc | tctcacggtt | cagtacccac | gcttcgaacg | agggatggga | 1260 |
| gcaggcgcca | cggccggcac | cccagagccc | tgctgcccct | tagttcgagc | ggccatcctc | 1320 |
| ctgtggggct | tgtgggcagc | ctgtgggtt | tgtgggcggc | ctgtgggtt | tgtgggtggt | 1380 |
| ctaaggaaag | agttggggca | ctcaggggtc | tgctgttttt | gcccgtggcc | ttaactcatc | 1440 |
| aggggagggt | ttctgcagca | gaatctcggg | ctcaggggtg | gcggttaacg | agggagcagc | 1500 |
| ggggtcttgg | ggaggggggct | cgacacccct | gaaggtgccc | cctaaaggag | ccactgttag | 1560 |
| aggggcaccc | catcttttgtg | gccatggcgg | tggtagagcg | gctgggaggg | gctctgcggc | 1620 |
| gagcaaggga | gcaggcggta | ggggttctgc | ggcgatgggc | gggctagggg | cggggcgcgg | 1680 |
| gtgggctcta | aaagtcggtg | cccactcgct | ccgcgctgcc | gcggcaacca | gcacaccccg | 1740 |
| gcacctcctc | tgcggcagct | gcgcctcgca | agcgcagtgc | cgcagcgcac | gccggagtgg | 1800 |
| ctgtagctgc | ccggcgcggc | gccgccctgc | gcgggctgtg | ggctgcgggc | tgcgccccg | 1860 |
| ctgctggcca | gctctgcacg | gctgcgggct | ctgcggcgcc | cggtgctctg | caacgctgcg | 1920 |
| gcgggcggca | tgggataacg | cggccatggt | gcgccgagat | cgcctccgca | ggtgagtgtg | 1980 |
| cggtgggaac | gaggggggtgt | ggctggcggc | cctgggacta | gggcgcaggc | gagcggagga | 2040 |
| ctgtgtgccc | gtgtccgagc | tggggctgcc | tctgggcgaa | aactctaccg | acaggcggca | 2100 |

```
cgcattccgc gcccgctctg cctacttgag gaggggtgt cactcctgcc cgcaatggaa      2160
tgttcagaac gcgggacctc cttgggttag gatttctaga ccccgggatc gtcgtggtga      2220
gatttaggat ttctggaccc cagcgtcatc ttgatatgac ttaggatcca taatgaccct      2280
ggtctcaccc tgatgcgaat tgggattttt agatcctggc atcaccctgg tgcgatttag      2340 gattttata ctcagtcatt gctgcagcat gatttaggat ttctaacccc cagcatcgcc       2400
ctggtttgat ttaggatatt tagactccgg cttccctctg gtgcgattca ggattcttag      2460
actccgccgt tgccgtggcg cgatttagga tttatagatc ccggcaaagc cctggtgcga      2520
tgtaggattt ttagaacccc agcatcgctc tggtgcgact taaaggatag gccccagcat      2580
cgccctggtg cgatgtagga tttttagaac cccggtgtct ccgtggcgca ccttaggatt      2640
tcaagaacgg gataatcgca gtgccgagat cgccgcggtg cagcttagga tttcaagacc      2700
caggtatcac ggtggcggga gtcaccgcag tgactagaac tcgcagtgcc cgtcagccgc      2760
cttaagtatt tttcagattt cagtaacaag cgcgagtgag aacggcgatg tgaccaaact      2820
gtcatgttgc gcagggattg ttcaccttgg tttcgcgggt tttcaaagtg gttcgtctcg      2880
cggcgacgcc atcaggtggg cggcaggttg ggtggtatta ttacgggagt gtgtttttct      2940
gtttacaaga tgaagaaatc aaggctcaga aattttggga aagtttgtta ctggagtttg      3000
cttattgtct ccgctcatgg ctcatcaaat agttgggatt ttggccaaaa atgtttgct       3060 taacccattt tgcctactga cggctaggtt gcttcacttc taaaaatcct aaaagttcat      3120
ggggcatttt ttactgaggt aataagacaa aaaatggccc cctgagaggt tgcctctttg      3180
ctttcttgga gtaagaggag gagggtgtgg aggggggtgt ccaggagtgg agtatgttgg      3240
tcgatagcct cgttttttaa cccccccactt tccctgagca gcggcgggga agcctcccca     3300
tttgccgctc tggccgcccc tcccggggct ctctgctgag tcactgcaga gattcagctg      3360
ctggaacccc ggggatgaat gcgatgagaa gcactgggggg aaaggagtaa tgaaatctgc     3420
acatgaaaat gtatacattg aagtacagga cagataggc tgggcaaatg atcgtcaaaa       3480
cctaatggtt tttgtcatct gacctttcaa ggagatactg gatacagcc tgctattgtt       3540 gggtgaaaac tgtgatataa ccatcatgtt ctggcacttt tttgaaccat ttctagtatt      3600
accttgagaa gtaggaccaa atggttctat ccgtcttatg gacaggtact ttggagaaaa      3660
aaagaaatga ctgccctaat aatgcctaaa aaatagcctg gggagctgac attgtttaag     3720
aaacatggtt attttaccac tgtaaaacca caggcttgtt tttagatttt agcaaaaagt      3780
atcagggata tggggggggaa aagtatcttg taagttgagg aagttagcga acgggtaggt    3840
agattacagg caatagggaa gaatgtgtgt acagacggaa agccatttcc cccagggctt     3900
tagcaattaa tttatttcag ctctatgaca actctaattt tagttttgga gggtattatt      3960
tccattctgg ctgttttgag agaacttcca ttctactgac aattcttgat ctgttgacca      4020
tcagaagtca tagacttgaa acagaacggt ttataattcc tgtttggcac tccttgtcaa     4080
tgtggataaa ctgacttgtg cctttgaagt cctgggcatg ggagggttgg gtgtaccaac      4140
cagtgctctt tttccaaaga caaaatcaat tctcacacgc tgggtatgag ttatgcctta      4200
tctgggggtg ggggagcatc ttaggaaatt aaatggaaac ttaaagagtc tgctaagaaa      4260
agcagaaatg taatctaccg ccttgacctc tcaagagatt agatattcag ggtcatgaca      4320
aagctgctta tgttggaata cacagtgcag ctatcttact ttcacagact gtttaccctg      4380
agcagtttct cagcccaaat ccagaaagga gtactaaatg gggcttcatt taggcaggag      4440
```

```
-continued ggctgaaaat caggagtagc tctctgcttg aggacatgtg ataagttact acacacacac    4500
actctttaaa acatgagata tagcacatat atattttttg aacattttac tggttggggg    4560
tagtgggtag atggtagagc ttttggagta aataagaaag aagttatttt tttcctggga    4620
agccttgata aaagtcaacg aaagagtgtc cagcatttaa gtcatgtccc ttttatttat    4680
ataaagtcct cttcagcagg tattgggaag accacaaggg taggggctaa ggggttaaag    4740
tcggggagca gaggcagaag attatatgtt gaaataatgt attttttttc cttaagatta    4800
gaatgatgaa caaatatggt gagtgctatg gcagacagag gtttgattat agtctcggtc    4860
agctttgtgc ctatgtgaag ggcaatgtaa tcattgcatg gtaacagcaa tctcccaccc    4920
catcttacca ggttttggtt tgtagatgag tggacaatgt tacctgactg cttacagtgg    4980
gtctctgctt ttcctacagg atg                                            5003

<210> SEQ ID NO 2
<211> LENGTH: 24
<212> TYPE: DNA
<213> ORGANISM: Human

<400> SEQUENCE: 2
ggttttaaaa gtcggtgttt attc                                             24

<210> SEQ ID NO 3
<211> LENGTH: 21
<212> TYPE: DNA
<213> ORGANISM: Human

<400> SEQUENCE: 3
aactacaacc actccgacgt a                                                21
```

NON-INVASIVE METHOD FOR THE EARLY DIAGNOSIS OF GASTRIC CANCER USING AS A BIOMARKER THE METHYLATION LEVELS IN THE DNA SEQUENCE OF MICRORNA-335-5P PROMOTER

BACKGROUND OF THE INVENTION

The invention is directed to a method of gastric cancer detection in samples of healthy population, obtained non-invasively and preferably from plasma. The method comprises the detection of methylation of the DNA sequence of the promoter region of the microRNA-335-5p, which is associated with multiple cellular processes involved in gastric cancer.

The present invention favors the early detection of gastric cancer, in a reliable, non-invasive way and at a lower cost, thus being available to a greater number of people in stages of diagnostic or treatment of gastric cancer.

Preferably, the invention consists of diagnosing the presence or absence of gastric cancer- a disease that is the third leading cause of cancer death in the world and first in Chile-in an early and non-invasive manner, preferably in plasma samples from healthy population.

Although the cumulative risk of gastric cancer precursor lesions is well known in the state of the art, as well as the emotional impact on people of the use of invasive methods in sampling, such as upper digestive endoscopy, for example; and the high cost of current diagnostic technologies, no rapid and easily accessible global strategies have been developed for early diagnosis and reduction of mortality due to gastric cancer. This situation creates the problem of the absence of methods having high detection sensitivity and rapid delivery of the results, but that are also non-invasive, so that they to allow early detection of gastric cancer and may be applicable to the general population.

MicroRNAs are a class of approximately 2603 known, non-coding RNAs, of about 24 nucleotides long, which inhibit, through binding to coding gene regulation sites, the gene expression of several genes that regulate in turn multiple cellular processes involved in cancer. According to the above, microRNAs have currently been involved in the regulation of various biological processes that are carried out in tumor cells, including cell proliferation, differentiation, migration and invasion guided by these cells.

Among the microRNAs associated with cancer is microRNA-335-5p (or simply miR-335), which is a transcript of the 7q32.2 chromosomal region, regulated by methylation of the DNA sequence of its upstream promoter. The miR-335 has been described as having both tumor suppressor activity and tumor promoter activity; however, its specific activity in gastric cancer has not been fully elucidated, thus so far there are no non-invasive diagnostic methods that use miR-335 as a marker.

In the closest prior state of art, different findings and technologies have been disclosed, which correlate microR-NAs with gastric cancer, but without advancing or suggesting a diagnostic alternative such as that of our invention. Similar methodologies that can be considered close to this invention are described in the documents summarized below: Hailong, Li, et al., (2014), WO2016022076. US2011177965, Zhang et al., (2017), Zhengrong Li, et al., (2014) and Ma, J., et al. (2013).

Hailong, Li, et al., (2014). The clinical significance of downregulation of mir-124-3p, mir-146a-5p, mir-155-5p and miR-335-5p in gastric cancer tumorigenesis. Int. J. of Oncology, 45(1): pgs. 197-208. This publication reports an alternative to detect the level of expression of microRNAs associated with gastric cancer cell lines, compared to non-cancer cells. This scientific study focuses its analysis on a population of total RNA extracted from cell line culture, without considering plasma samples or less still measuring the methylation of the promoter regions of the DNA that encodes such microRNAs.

WO2016022076 (TOO HENG-PHON, et al). This publication refers to an alternative to quantify the expression of various microRNAs, with the aim of employing them as markers of gastric cancer. Among the 191 microRNAs detected in serum and/or plasma, miR-335 is included (table 4); however, there is no correlation between the expression of miR-335 among cancer patients versus healthy patients, and in addition, the detection of the expression is through RT-PCR of total RNA samples, without disclosing or suggesting the assessment of methylation of the promoter regions of the DNA encoding miR-335.

US2011177965 (Hoshen Moshe et al.). This publication refers to the quantification of microRNAs, which can be used as markers of gastric cancer and which are identified with nucleotide sequences N°s1-46: however, the use of miR-335 promoter coding sequences is not disclosed. This document also quantifies by RT-PCR from a sample of total RNA extracted from cancer tissue, without referring to the possible assessment of the methylation of the promoter regions of the DNA encoding each microRNA.

Zhang et al., (2017). Up-regulation of CRKL by microRNA-335 methylation is associated with poor prognosis in gastric cancer. Cancer Cell Int., 17:28. This document quantifies the expression of miR-335 and its role in gastric cancer, and the authors conclude that miR-335 is a tumor suppressor, and that its expression is turned off, by hypermethylation of its promoter. Zhang et al., similar to the invention presented here, also uses MSP to measure the methylation in the miR-335 promoter and uses it as a predictive tool for gastric cancer. However, the analyses are performed on tissue samples from patients with gastric cancer and cell lines, without considering the analysis from the patients' plasma, where circulating levels of the miR-335 promoter DNA are also present from the initial stages of the illness.

Zhengrong Li, et al., (2014). Methylation-associated silencing of MicroRNA-335 contributes tumor cell invasion and migration by interacting with RASA1 in gastric cancer. Am. J. Cancer Res. 4(6): 648-62. This scientific report bases its research on the quantification of miR-335 expression and its role in gastric cancer. As part of the quantification tools, MSP is also used to measure the methylation in the miR-335 promoter methylation, which Zhengrong Li, et al. conclude can be used in conjunction with the expression of miR-335, as epigenetic markers of gastric cancer and suggests it as a predictive tool for gastric cancer: however, analyses are performed only on samples of cell lines or total DNA and are limited to considering in isolation but without demonstrating, the alternative of measuring the circulating levels of the microRNA in plasma, and without including or suggesting the analysis of the methylation state of the nucleotide sequence of the circulating promoter in the plasma.

Ma, J., et al. (2013). Quantification of plasma miRNAs by digital PCR for Cancer Diagnosis. Biomark Insights 8:127-36. This document bases its research on the quantification of microRNAs in plasma, as possible biomarkers of lung cancer, being able to detect miR-335-3p, using "digital PCR". This publication does not consider the analysis of gastric cancer biomarkers, nor does it consider measuring the levels of methylation of the promoter regions of the DNA conding for any microRNA.

Among those systems described in the documents that have just been summarized, which in our opinion constitute the closest prior state of the art, sufficient information about miR-335 and its participation in the evolution of various types of cancer has been disclosed, to the point of being considered, a possible biomarker of some types of cancer, gastric cancer among them, as can be seen, moreover, from the invention proposed in this application.

However, in the state of art prior to this invention, the determination of miR-335 expression levels and their link with gastric cancer are mainly based on RNA levels measured by RT-qPCR, and with samples from carcinogenic tissue and/or gastric cancer cell lines, which requires a clinical intervention in the people in order to extract the sample to be analyzed, which is not only an invasive and high-cost procedure, but also requires more time for the sampling process and thus, for obtaining the results.

The prior art does not show evidence of being able to detect—far from its production point—a molecule with low levels of circulating concentration and that is also upstream of the expression of microRNA-335-5p, thus, the possibility of contributing to the public health a non-invasive, low-cost diagnostic alternative, capable of detecting the development of cancer even at an earlier stage than the beginning of the imbalance in the levels of microRNA-335-5p is not offered.

Prior to the invention presented here, there has been no disclosed publication reporting the detection of the state of miR-335 expression in samples that have not been extracted from invasively isolated tissues, such as biopsies for example. This basically due to the low probability of detecting an RNA molecule, which per se is highly unstable, and which must also be found far from its expression environment, such in blood for example, for its non-invasive detection, and which must undergo two subsequent stages of manipulation for its analysis (plasma preparation and tuning of the detection system).

RNA's own instability contributes to the low proportion of these molecules reaching blood circulation, once expressed in the tissue affected by gastric cancer, which is why the possibility of detecting miR-335 in plasma is difficult and unstable.

To the above, it should be added that according to what the inventors of this application have been able to establish, the appearance of gastric cancer is associated with the inhibition of the expression of miR-335, thus, in states of disease onset, miR-335 plasma levels should be even lower, since its expression is inhibited, making it more difficult to detect miR-335 and to use it as a marker of gastric cancer in plasma.

Given the difficulty and, at the same time the need, for an early, low-cost and non-invasive gastric cancer diagnostic system, the inventors have focused on solving this problem as part of their research at the Pontifical Catholic University of Chile, and have achieved the necessary conditions to establish the state of development of a gastric cancer, by analyzing the circulating levels of methylated free DNA from the nucleotide sequence of the promotor region of the microRNA-335-5p in non-invasive samples, mainly in plasma.

The evaluated region was verified to correspond to the promoter region of the MEST gene through the online program PROSCAN Version 1.7 (BioInformatics and Molecular Analysis Section, NIH), (https://www-bimas.cit.nih.gov/molbio/proscan/). bp, base pairs The following table summarizes the prediction results.

| CpG Islands | Size of the CpG island (bp) | Start-end of the CpG island (bp) |
| --- | --- | --- |
| CpG Island 1 | 318 | 460-777 |
| CpG Island 2 | 465 | 836-1300 |
| CpG Island 3 | 757 | 1546-2302 |
| CpG Island 4 | 584 | 2362-2945 |

Figure 2:
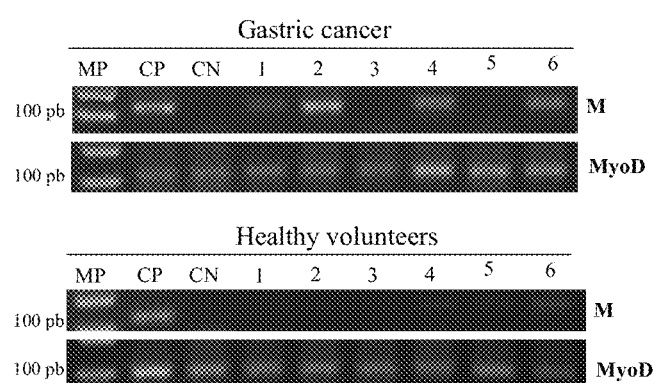

FIG. 2 summarizes the results found in three independent experiments in plasma from patients with gastric cancer versus healthy people, applying MSP according to the invention. MyoD was used as a DNA conversion control; M, PCR product with specific primers for DNA methylation; CP corresponds to the positive control of methylation (methylated gastric cancer cell line); CN corresponds to the negative control of methylation (peripheral blood lymphocytes).

DETAILED DESCRIPTION OF THE INVENTION

The invention is directed to a non-invasive method of early diagnosis of gastric cancer, using as a biomarker the levels of methylation of the DNA sequence of the microRNA-335-5p promoter in plasma.

Specifically, the invention presented here is a method for the early detection of gastric cancer, by detecting the increase in DNA methylation of the promoter region of microRNA-335-5p in samples obtained non-invasively, preferably in plasma. Thus, it is a contribution for the early detection of gastric cancer, without invasive procedures, with rapid collection of the sample and delivery of the results, and of lower cost than the technologies that employ invasive diagnostic techniques to the human body and animal body in general.

MicroRNA-335-5p (miR-335) is a transcript located on chromosome 7q32.2, in the second intron of the MEST gene (Mesoderm Specific Transcript Homolog), which codes for 17 different mRNAs, which can be transcribed from multiple transcription initiation sites, controlled by chromosomal methylation of CpG islands. The mature sequence of miR-335 in humans corresponds to 16-UCAAGAGCAAUAACGAAAAAUGU-38 (http://www.mirbase.org, accession: MIMAT0000765, ID: hsa-miR-335).

The promoter region of miR-335 is considered 5000 bp upstream of the start of transcription (ATG) and is shown in SEQ ID No. 1.

The inventors have determined that microRNA-335-5p is a potential tumor suppressor gene in gastric cancer and that it is rendered inactive by DNA methylation in its promoter region. Based on this result and on the need for a reliable biomarker that is fast to quantify at low concentrations from non-invasively isolated samples and that is low cost to people, the method of the invention, which allows for early detection of the development of gastric cancer, was developed; this, since surprisingly the inventors have established that determining the degree of DNA methylation of the promoter region of microRNA-335-5p in plasma allows to correlate an increase in said degree of methylation within patients with gastric cancer in comparison to healthy population.

Studies developed by the inventors show that patients with gastric cancer have high levels of methylation compared to the levels observed in healthy subjects from the general population.

Figure 1:
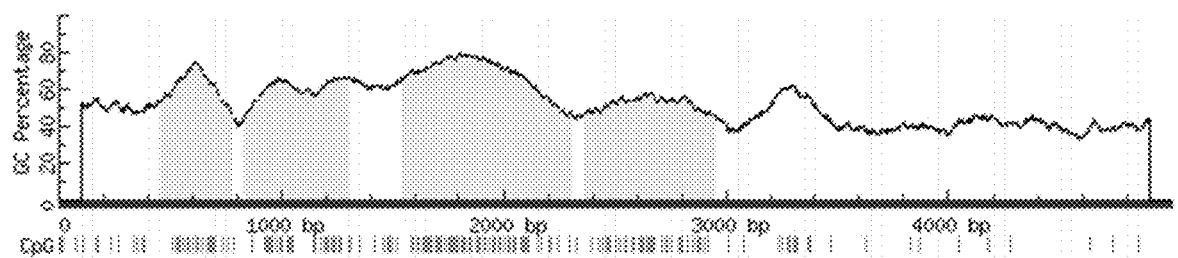
FIG. 1 corresponds to a prediction scheme of the CpG islands of the promoter region of the MEST gene for microRNA-335-5p. Four CpG islands of the genomic region are observed 5000 bp upstream of the translation site. The parameters used for the prediction were: CpG island size=200 bp, % GC=50%, observed/expected CpG ratio=0.6. For the prediction, the Methprimer 2.0 online platform was used (http://www.urogene.org/cgi-bin/methprimer2/MethPrimer.cgi).

FIG. 1 shows the regions susceptible to being methylated in the sequence of the promoter region of microRNA-335-5p. It will be obvious to the person skilled in the art that different regions within this promoter can be detected in order to establish their degree of methylation, and thus be used in the method of the present invention. As indicated in the description of the figure, four CpG islands of the genomic region are observed, so that conveniently the method of the invention aims at detecting promoter methylation within these 4 zones.

Thus, the invention contributes to the state of the art, the detection of methylated DNA from the promoter region of microRNA-335-5p as a biomarker of gastric cancer, in non-invasively obtained samples, preferably from plasma, where an increase in levels of said methylated DNA, is indicative of a developing gastric cancer. While low circulating levels of methylated DNA from said promoter region of microRNA-335-5p, it is indicative of an absence of disease or very early stages of this cancer.

Thus, the invention overcomes previously unsolved limitations in the current state of art, such as providing methods of gastric cancer diagnostics methods characterized by being non-invasive, highly accurate, fast in the delivery of results and of low purchase and operational cost.

The method of detecting the methylated DNA sequence comprising the promoter of microRNA-335-5p expression can be detected by any means available in the art, such as Polymerase Chain Reaction for Methylated Sequences (MSP), quantitative MSP, expression microarrays, bisulfite sequencing, or pyrosequencing.

In one embodiment, the invention resolves the previously stated limitations by employing PCR or MSP-specific methylation primers that specifically allow detection of low concentration levels of the methylated DNA sequence of the miR-335 promoter.

If a PCR technique for methylated sequences is chosen for the embodiment of the invention, the primers can be designed for any region of the promoter containing a methylation site, preferably one of the four CpG islands defined in FIG. 1.

All possible embodiments for the detection of the methylated sequence of this promoter are comprised within the scope of the present invention.

As indicated, in the prior art, the expression of miR-335 has mainly been detected by the detection of a 24-nucleotide long RNA, with all the difficulties that RNA detection brings, mainly due to its tendency to degradation in samples. On the contrary, the method of the invention focuses on the DNA of the promoter region of said RNA. As DNA is more resistant to degradation than RNA, our invention also provides greater stability over time and in the storage of its components, as well as of the sample to be analyzed, which, since it is obtained non-invasively (preferably plasma), is easily accessible, and this further reducing costs and increasing public accessibility to both diagnosis and early curative treatments.

Next, a preferred embodiment of the invention is described, without limiting the technical variants that an expert in the field can incorporate or modify, and which are within the scope of the inventive concept that we claim in this application.

EXAMPLES

The plasma was obtained using conventional techniques, which (0.5-1 ml) were used to extract DNA from 41 patients with gastric cancer and from 30 healthy donors, using the "QIAamp DNA Mini Kit" according to the indications of suppliers (QIAGEN, USA). The extracted DNA was dissolved in 20 μL TE buffer and bisulfite conversion was performed using the EZ DNA Methylation-Gold™ Kit reagents (Zymo Research Corporation, Irvine, Calif., USA).

The specific PCR for methylated DNA (MSP) of the miR-335 promoter was performed according to the procedure of Zhengrong Li, et al. (2014), using the primers that amplify the second CpG islet between bases 1683 and 1808 of said promoter:

Primer1(forward):SEQ ID No.2;

Primer2(reverse):SEQ ID No.3.

The conditions of the MSP were: denaturation 3 min. at 95° C., followed by 35 cycles of 30 sec. at 95° C., 30 sec. at 52° C. and 40 sec. at 72° C. The experiments were performed three times independently. The reported results represent the best combination of 3 pairs of primers evaluated for the miR-335 promoter region. The other evauluated sequences had sensitivity and specificity problems for determination in plasma.

The results showed positive amplification bands in 23 of 41 (56.1%) plasma samples from patients with gastric cancer, but only in 9 of 30 (27.8%) plasma samples from healthy donors, thus, being the observed difference significant, (p=0.029, Pearson's correlation).

FIG. 2 summarizes the results found in three independent plasma experiments of patients with gastric cancer versus healthy people, applying the MSP method according to the invention.

This figure shows the "M" amplification, which corresponds to the result of the PCR product with specific primers for DNA methylation of the sequence comprising the promoter of the expression of microRNA335; and MyoD, an internal and constitutive marker in plasma was used as a DNA conversion control. CP corresponds to the positive control of methylation (methylated gastric cancer cell line); CN corresponds to the negative control of methylation (peripheral blood lymphocytes).

As can be seen, a strong degree of methylation of this region is seen in 4 of the 6 patients with gastric cancer, while in healthy volunteers a low degree of methylation is seen only in 2 cases (lanes 4 and 6).

In this way, it is found that an increase in the methylation of the miR-335 promoter region in plasma can be correlated with the presence of gastric cancer. Where, the method of the invention can be used by itself or in combination with other biological markers for the early detection of gastric cancer in plasma samples from an individual.

The invention claimed is:

1. A method for detecting a concentration of methylated DNA of a promoter of microRNA-335-5p in plasma, comprising:

obtaining a sample of the plasma from a live subject in a non-invasive manner;

adding one or more primers to the sample, wherein the one or more primers amplify a CpG island of the promoter of microRNA-335-5p, said CpG island defined from base 1683 to base 1808 of SEQ ID No. 1;

after adding the one or more primers, performing polymerase chain reaction (PCR) cycles on the sample; and after performing the PCR cycles, detecting positive amplification bands in the sample, wherein the primers include a forward primer having a sequence of SEQ ID No. 2 and a reverse primer having a sequence of SEQ ID No. 3.

2. The method of claim 1, wherein the PCR cycles each include 30 seconds at 95° C., 30 sec. at 52° C. and 40 sec. at 72° C.

3. The method of claim 2, wherein 35 of the PCR cycles are performed.

* * * * *